June 22, 1965 G. DE RUITER Plant Pat. 2,540
ROSE PLANT
Filed March 11, 1964
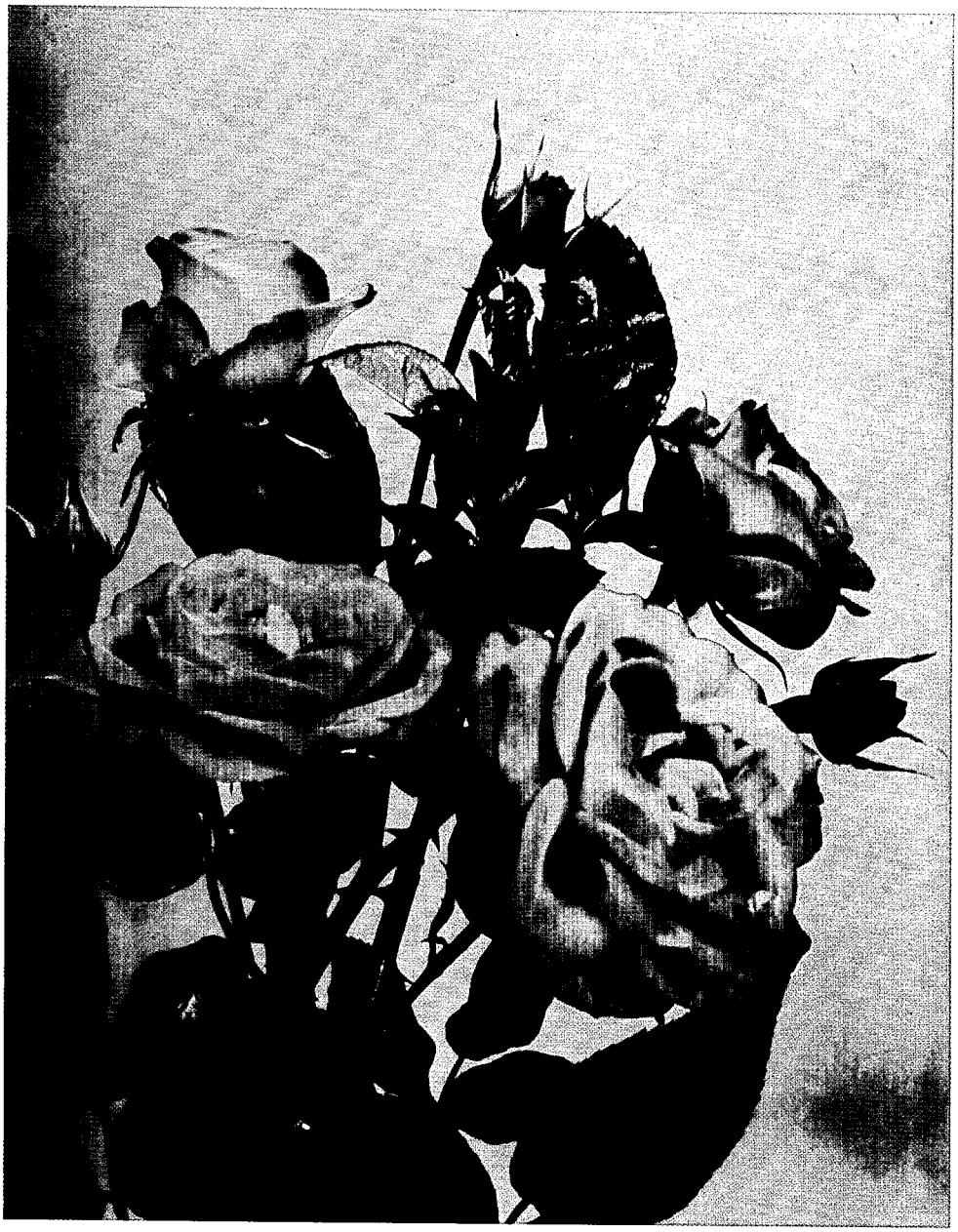
Inventor.
Gerrit de Ruiter
By: Robb & Robb
Attorneys.

United States Patent Office

Plant Pat. 2,540
Patented June 22, 1965

2,540
ROSE PLANT

Gerrit de Ruiter, Hazerswoude, Netherlands, assignor to The Conard-Pyle Company, West Grove, Pa., a corporation of Pennsylvania Filed Mar. 11, 1964, Ser. No. 351,264
1 Claim. (Cl. Plt.—28)

The present invention relates to a new and distinct variety of rose plant of the floribunda class, which was originated by me by crossing the variety known in Holland as "Ruth Leuwerik" (unpatented) with the variety known as "Rosemary Rose" (unpatented).

As the result of this breeding, I have produced a new rose variety which is definitely distinguished from its parents, as well as from all other varieties of which I am aware, as evidenced by the following unique combination of features which are outstanding therein:

(1) A compact and well-branched habit of growth;
(2) Leathery dark green foliage;
(3) Good petalage (numbering 25 to 28 petals) and regular arrangement of the petals;
(4) A distinctive and attractive general color tonality of the flowers corresponding to an intense, velvety, luminescent Chrysanthemum Crimson color;
(5) A slight tea flower fragrance; and
(6) Exceptionally good flower longevity as cut flowers, which exceeds that of any other variety known to me.

Asexual reproduction of the new variety by budding, as performed by me in Holland, and as performed at West Grove, Pennsylvania, U.S.A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Color Chart of the Royal Horticultural Society, except where general color terms of ordinary dictionary significance are obvious:

Type: Hardy; bush; outdoor; seedling; for garden decoration.
Class: Floribunda.
Breeding: Seedling.
*Seed parent.*—"Ruth Leuwerik."
*Pollen parent.*—"Rosemary Rose."
Propagation: Holds its distinguishing characteristics through succeeding propagations by budding.

*Flower*

Locality where grown and observed: West Grove, Pennsylvania, U.S.A.
Flowers borne: Several to stem; in regular pyramidal clusters; on stems of medium length and normal strength.
Quantity of bloom: Abundant, outdoors.
Continuity: Continuous.
Fragrance: Slight. Nature—tea.
Bud:
*Peduncle.*—Medium length; slender; erect; stiff; rough; with numerous glandular tipped red hairs. Color—reddish.
*Before calyx breaks.*—Size—small. Form—ovoid; with a conspicuous neck; with foliaceous appendages on the surface of the bud; with stout, much-cut foliaceous parts extending beyond the tip of the bud equal to ½ or more of its length.

*As calyx breaks.*—Color—Indian Lake, Plate 826.
*As first petal opens.*—Size—medium. Form—medium length; square. Color: outside—Cardinal Red, Plate 822, usually shaded in places with Indian Lake, Plate 826; inside—near Chrysanthemum Crimson, Plate 824, but lighter and with an apparent underlying luminescence.
*Opening.*—Opens up well.
Bloom:
*Size (when fully open).*—Medium; from 3 inches to 3¾ inches.
*Petalage.*—Double; from 25 to 28 petals; arranged regularly.
*Form.*—Cupped at first and remaining cupped; petals being at first almost flat and remaining almost flat at maturity.
Petals:
*Texture.*—Medium thickness.
*Appearance.*—Inside—velvety. Outside—shiny.
*Shape.*—Outer—roundly ovate; with one notch. Intermediate—roundly ovate; with one notch. Inner—ovate; with one notch.

This description of a newly opened flower was made from a rose grown outdoors in the month of October at West Grove, Pennsylvania, U.S.A.:

*Color.*—Outer petal: outside surface—Cardinal Red, Plate 822, with irregular shadings of Indian Lake, Plate 826; inside surface—near Chrysanthemum Crimson, Plate 824, but appearing lighter due to an underlying velvety luminescence; often with a greenish white streak radiating from the point of attachment. Intermediate petal: outside surface—China Rose, Plate 024 over main body of petal, with outer margin Cardinal Red, Plate 822; inside surface—near Chrysanthemum Crimson, Plate 824, but lighter due to an underlying luminescence and becoming tinted with Persian Rose, Plate 628/1 at base of petal. Inner petal: outside surface—China Rose, Plate 024 over main body of petal, but darker along upper margin; inside surface—near Rose Red, Plate 724, but darker and with a velvety luminescence, and with base of petal tinted with Persian Rose, Plate 628/1.

This description was made from a rose that was open for three days outdoors in the month of October at West Grove, Pennsylvania, U.S.A.:

*Color.*—Outer petal: outside surface—Chrysanthemum Crimson, Plate 824, overlaid with Oxblood Red, Plate 00823/2.; inside surface—Chrysanthemum Crimson, Plate 824, but somewhat lighter due to an underlying velvety luminescence. Inner petal: outside surface—China Rose, Plate 024, shaded with Cardinal Red, Plate 822, around upper margin; inside surface—near Rose Red, Plate 724, but slightly darker and with a velvety sheen.
*General color effect.*—Newly opened flower—near Chrysanthemum Crimson, Plate 824, with color made more intense by an underlying velvety luminescence. 3-days open—near Chrysanthemum Crimson, Plate 824, but with color lightened and intensified by an underlying velvety luminescence.
*Behavior.*—Drop off cleanly.
*Flower longevity.*—On bush in garden—7 days in October. Cut roses grown outdoors and kept at living room temperatures—10 days in October.

*Reproductive organs*

Stamens: Medium number; arranged regularly about pistils; mixed with petaloids.

Filaments: Some medium and some long; most with anthers. Color—pink, with whitish-yellow base.
Anthers: Small size; all open at once; occasionally an anther fused with a petaloid. Color—dark brown.
Pollen: Moderate quantity. Color—gold.
Pistils: Medium number.
Styles: Uneven; medium length; medium caliper; bunched.
Stigma: Color—pale yellow.
Ovaries: All enclosed in receptacle.
Hips: Globular; with inconspicuous neck; smooth; walls medium thick and dry. Color—reddish.
Sepals: Permanent; moderately long; straight; spear-shaped.
Seeds: Few; small.

*Plant*

Foliage:

*Leaves.*—Compound of 5–7 leaflets; abundant; moderately large; leathery.

*Leaflets.*—Shape—oval, with apex acute. Base—obtuse. Margin—simply serrate.

*Color.*—Mature: upper surface—Ivy Green, Plate 0001060; under surface—Sage Green, Plate 000861/1. Young: Upper surface—Maroon, Plate 1030; under surface—Sage Green, Plate 000861/1, overlaid with Erythrite Red, Plate 0027.

*Rachis (the supporting stem of the compound leaf).*—Medium caliper. Upper side—hairy. Under side—sparsely prickly.

*Stipules.*—Medium length; medium width; with moderately long points turning out at an angle of 45°.

*Disease resistance.*—Comparable to that of the average variety grown under the same cultural conditions at West Grove, Pennsylvania, U.S.A.

Growth:

*Habit.*—Bushy; much-branched.

*Growth.*—Vigorous.

*Canes.*—Medium caliper.

*Main stems.*—Dull. Color—Parsley Green, Plate 00962/1. Prickles—several; color—brown. Hairs—none.

*Branches.*—Dull. Color—Parsley Green, Plate 00962/1. Prickles—several; color—reddish brown. Hairs—none.

*New shoots.*—Dull. Color—Fern Green, Plate 0862, overlaid with Erythrite Red, Plate 0027. Prickles—several; color—reddish. Hairs—none.

I claim:

A new and distinct variety of rose plant of the floribunda class, substantially as herein shown and described, characterized particularly as to novelty by the unique combination of a compact and well-branched habit of growth, leathery dark green foliage, good flower petalage and regular arrangement of the petals, a distinctive and attractive general color tonality of the flowers corresponding to an intense, velvety, luminescent Chrysanthemum Crimson color, a slight tea flower fragrance, and especially good flower longevity as cut flowers.

No references cited.

ABRAHAM G. STONE, *Primary Examiner.*